(12) United States Patent
Gao et al.

(10) Patent No.: US 9,949,973 B2
(45) Date of Patent: Apr. 24, 2018

(54) ACOUSTIC MIXING FOR AUTO GRANULATION

(71) Applicant: AbbVie Inc., North Chicago, IL (US)

(72) Inventors: Ping X Gao, Highland Park, IL (US); Raimundo Ho, Glenview, IL (US); Jayanthy Jayanth, Buffalo Grove, IL (US); Samrat Mukherjee, Grayslake, IL (US); Katherine E. Peterson, Wadsworth, IL (US); John C. Strong, Lindenhurst, IL (US); Ping Tong, Potomac, MD (US); Geoff G. Zhang, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 15/204,217

(22) Filed: Jul. 7, 2016

(65) Prior Publication Data
US 2017/0007600 A1     Jan. 12, 2017

Related U.S. Application Data

(60) Provisional application No. 62/189,677, filed on Jul. 7, 2015.

(51) Int. Cl.
| | | |
|---|---|---|
| *A61K 31/505* | (2006.01) | |
| *A61J 3/02* | (2006.01) | |
| *A61K 9/16* | (2006.01) | |
| *B01F 11/02* | (2006.01) | |

(52) U.S. Cl.
CPC .............. *A61K 31/505* (2013.01); *A61J 3/02* (2013.01); *A61K 9/1688* (2013.01); *B01F 11/02* (2013.01); *B01F 2215/0032* (2013.01)

(58) Field of Classification Search
CPC . A61K 31/505; A61K 9/16; A61J 3/02; B01F 15/00

See application file for complete search history.

(56) References Cited

U.S. PATENT DOCUMENTS

| | | |
|---|---|---|
| 3,275,787 A | 9/1966 | Newberry |
| 2009/0168590 A1 | 7/2009 | Koenig et al. |

FOREIGN PATENT DOCUMENTS

| | | | |
|---|---|---|---|
| EP | 2042232 A1 | | 4/2009 |
| WO | 2014/078258 A1 | * | 5/2014 |

OTHER PUBLICATIONS

Juan Guillermo Osorio Caicedo., Dissertation Abstracts International, (2014) vol. 76, No. 2B E. Order No. AAI3643325. 270 pages. ISBN: 978-1-321-30795-5.*

International Search Report and Written Opinion for Application No. PCT/US2016/041275, dated Nov. 14, 2016, 7 pages.

Mullarney, M.P., et al., "Applying Dry Powder Coatings," Pharmaceutical Technology, Oct. 2, 2011, 4 pages.

* cited by examiner

*Primary Examiner* — Alexander R Pagano
*Assistant Examiner* — Ebenezer O Sackey
(74) *Attorney, Agent, or Firm* — Neal, Gerber & Eisenberg LLP

(57) ABSTRACT

A process for acoustically mixing a bulk drug substance involves the application of acoustic energy to drive an accelerative force in a mixing vessel containing the drug substance. The drug substance may be, for example, Elagolix.

26 Claims, 1 Drawing Sheet

ACOUSTIC MIXING FOR AUTO GRANULATION

CROSS REFERENCE TO RELATED APPLICATIONS

This application claims the benefit of priority under 35 U.S.C. § 119 of U.S. Provisional Application 62/189,677, filed Jul. 7, 2015, which is incorporated herein by reference in its entirety.

BACKGROUND

Acoustic mixing technology has recently been introduced as an alternative mixing technology for powders and liquids that allows for rapid, uniform dispersion of material. This process operates on the principle of resonance where low frequency, acoustic energy creates a homogenous shear field within a mixing vessel, and the energy is transferred directly to the material to produce a consistent mixture without impellers or other additional mixing aids. This technology has been successfully applied to dry powder coating of drug particles having small particle size. The dry powder coating is often accomplished by co-mixing with nanosized inert substances such as $SiO_2$ where the admixture has improved surface properties resulting in improved processability. However, significantly less is known about the effect of acoustic mixing technology on drug particles having small size without the use of a co-additive such as $SiO_2$. Described herein is the discovery that certain pharmaceutical products can be acoustically granulated without additional additives such as $SiO_2$ or other granulation aids (such as water and polymeric binders), leading to substantially improved drug properties and processability. This discovery represents a significant advance in the arts of dry powder formulation for particularly challenging drug substances as it does not require co-milling with inert(s) nor acoustic mixing with such inert(s).

SUMMARY

In certain embodiments, this present disclosure comprises a process of acoustically mixing a bulk drug substance wherein said drug substance is substantially free of pharmaceutical excipients.

In embodiments, the acoustic mixing comprises the application of acoustic waves sufficient to subject the mixing vessel containing the drug substance to an accelerative force of greater than 10 G.

For example, in embodiments, the G-force is greater than 20 G, or greater than 30 G, or 40 G, or 50 G, or 60 G, or 70 G, or 80 G, or 90 G, or 100 G, or between 50 G and 100 G, or between 60 G and 90 G, or between 60 G and 80 G, or about 77 G, or about 85 G.

In embodiments, the G-force is greater than 20 G.
In embodiments, the G-force is greater than 30 G.
In embodiments, the G-force is greater than 40 G.
In embodiments, the G-force is greater than 50 G.
In embodiments, the G-force is greater than 60 G.
In embodiments, the G-force is greater than 70 G.
In embodiments, the G-force is greater than 80 G.
In embodiments, the G-force is greater than 90 G.
In embodiments, the G-force is greater than 100 G.
In embodiments, the G-force is between 50 G and 100 G.
In embodiments, the G-force is between 60 G and 80 G.
In embodiments, the G force is about 77 G.
In embodiments, the G-force is about 85 G.

In certain embodiments, said drug substance comprises an amorphous solid. In some embodiments, said drug substance comprises at least 50% w/w of an amorphous solid.

In some embodiments, said drug substance comprises at least 75% of an amorphous solid.

In some embodiments, said drug substance comprises at least 90% of an amorphous solid.

In some embodiments, said drug substance comprises at least 95% of an amorphous solid.

In some embodiments, said drug substance comprises at least 99% of an amorphous solid.

In some embodiments, said drug substance comprises at least 99.5% of an amorphous solid.

In certain embodiments, prior to acoustic mixing, the drug substance has a flowability constant (ffc) of less than 5.

In certain embodiments, prior to acoustic mixing, the drug substance has a flowability constant (ffc) of less than 2.

In certain embodiments, prior to acoustic mixing, the drug substance has a flowability constant (ffc) of between 2 and 0.3.

In some embodiments, prior to acoustic mixing, the drug substance has a bulk density of less than 0.4 g/mL.

In some embodiments, prior to acoustic mixing, the drug substance has a bulk density of less than 0.3 g/mL.

In some embodiments, prior to acoustic mixing, the drug substance has a bulk density of less than 0.2 g/mL.

In some embodiments, prior to acoustic mixing, the drug substance has a bulk density of between 0.2 g/ml and 0.05 g/ml.

In embodiments, prior to acoustic mixing, the drug substance has a bulk density of from between less than 0.3 g/mL and more than 0.05 g/mL.

In embodiments, acoustic mixing according to the instant disclosure increases the bulk density of the drug substance by at least 0.05 g/mL, such as at least 0.07 g/mL, or at least 0.1 g/mL, or at least 0.15 g/mL, or at least 0.16 g/mL, or at least 0.17 g/mL, or at least 0.18 g/mL, or at least 0.19 g/mL, or at least 0.2 g/mL, or at least 0.3 g/mL, or at least 0.4 g/mL, or at least 0.5 g/mL. For example, in embodiments, following acoustic mixing according to the instant disclosure, the bulk density of the drug substance is increased by an amount within the range of from about 0.03 to about 0.7, such as from about 0.04 to about 0.6, or from about 0.05 to about 0.2 g/mL, or from about 0.07 to about 0.19 g/mL, or about 0.1 to about 0.15 g/mL. For example, in embodiments, after acoustic mixing, the drug substance has a bulk density of from 0.2 to about 0.5 g/mL, such as from about 0.22 to about 0.35 g/mL, or from about 0.24 to about 0.3 g/mL. In embodiments, after acoustic mixing, the drug substance has a bulk density of greater than about 0.2 g/mL, such as greater than about 0.25 g/mL, or greater than about 0.3 g/mL.

In embodiments, acoustic mixing according to the instant disclosure increases the bulk density of the drug substance by at least 10% relative to the initial bulk density of the drug substance (prior to acoustic mixing). In embodiments, acoustic mixing according to the instant disclosure increases the bulk density of the drug substance by at least 20% relative to the initial bulk density prior to mixing. In embodiments, acoustic mixing according to the instant disclosure increases the bulk density of the drug substance by 30% relative to the initial bulk density of the drug substance prior to acoustic mixing. In embodiments, acoustic mixing according to the instant disclosure increases the bulk density of the drug substance by 40% relative to the initial bulk density of the drug substance prior to acoustic mixing. In embodiments, acoustic mixing according to the instant disclosure increases the bulk density of the drug substance by 50% relative to the initial bulk density of the drug substance prior to acoustic mixing. In embodiments, acoustic mixing according to the instant disclosure increases the bulk density of the drug substance by 60% relative to the initial bulk density of the drug substance prior to acoustic mixing. In embodiments, acoustic mixing according to the instant disclosure increases the bulk density of the drug substance by 70% relative to the initial bulk density of the drug substance prior to acoustic mixing. In embodiments, acoustic mixing according to the instant disclosure increases the bulk density of the drug substance by 80% relative to the initial bulk density of the drug substance prior to acoustic mixing. In embodiments, acoustic mixing according to the instant disclosure increases the bulk density of the drug substance by 90% relative to the initial bulk density of the drug substance prior to acoustic mixing. In embodiments, acoustic mixing according to the instant disclosure increases the bulk density of the drug substance by 100% relative to the initial bulk density of the drug substance prior to acoustic mixing. In embodiments, acoustic mixing increases the bulk density of the drug substance by 200% relative to the initial bulk density. In embodiments, acoustic mixing increases the bulk density of the drug substance by 300% relative to the initial bulk density. For example, in embodiments, acoustic mixing according to the instant disclosure raises the bulk density of the drug substance from about 25% to about 150% relative to the initial bulk density prior to mixing, such as from about 30% to about 125%, or from about 40% to about 110% relative to the initial bulk density prior to mixing.

In certain embodiments, prior to acoustic mixing, the drug substance has a volume-averaged particle size DV10 of less than 100. The term "particle size" refers, for example, to the size of a particle or agglomeration of particles.

In certain embodiments, prior to acoustic mixing, the drug substance has a volume-averaged particle size DV10 of less than 50.

In certain embodiments, prior to acoustic mixing, the drug substance has a volume-averaged particle size DV10 of less than 20.

In certain embodiments, acoustic mixing of the drug substance increases the volume-averaged particle size DV10 by at least 10 um.

In certain embodiments, acoustic mixing of the drug substance increases the volume-averaged particle size DV10 by at least 25 um.

In certain embodiments, acoustic mixing of the drug substance increases the volume-averaged particle size DV10 by at least 50 um.

In certain embodiments, acoustic mixing of the drug substance increases the volume-averaged particle size DV10 by at least 100 um.

In certain embodiments, acoustic mixing of the drug substance increases the volume-averaged particle size DV10 by at least 150 um.

In certain embodiments, acoustic mixing of the drug substance increases the volume-averaged particle size DV10 by at least 200 um.

In certain embodiments, prior to acoustic mixing, the drug substance has a flowability constant (flow function coefficient, or ffc) of less than 3 and subsequent to mixing greater than 3.

In certain embodiments, prior to acoustic mixing, the drug substance has a flowability constant (ffc) of less than 2 and subsequent to mixing greater than 2.

In certain embodiments, prior to acoustic mixing, the drug substance has a flowability constant (ffc) of less than 1 and subsequent to mixing greater than 1.

In some embodiments, acoustic mixing increases the flowability constant (ffc) by at least 0.1, 0.2, 0.3, 0.4, 0.5, 0.6, 0.7, 0.8, 0.9, 1.0, 1.1, 1.2, 1.5, 2.0, 2.5, 4.0, 7, 10, 12, or 15.

In embodiments, the flowability constant is increased by at least 0.1.

In embodiments, the flowability constant is increased by at least 0.2.

In embodiments, the flowability constant is increased by at least 0.3

In embodiments, the flowability constant is increased by at least 0.4.

In embodiments, the flowability constant is increased by at least 0.5.

In embodiments, the flowability constant is increased by at least 0.6

In embodiments, the flowability constant is increased by at least 0.7

In embodiments, the flowability constant is increased by at least 0.8

In embodiments, the flowability constant is increased by at least 0.9.

In embodiments, the flowability constant is increased by at least 1.

In embodiments, the flowability constant is increased by at least 1.1.

In embodiments, the flowability constant is increased by at least 1.2.

In embodiments, the flowability constant is increased by at least 1.5.

In embodiments, the flowability constant is increased by at least 2.0.

In embodiments, the flowability constant is increased by at least 2.5.

In embodiments, the flowability constant is increased by at least 4.0.

In embodiments, the flowability constant is increased by at least 7.

In embodiments, the flowability constant is increased by at least 10.

In embodiments, the flowability constant is increased by at least 12.

In embodiments, the flowability constant is increased by at least 15.

In certain embodiments, said drug substance is Elagolix.

In some embodiments, said drug substance is the monosodium salt of Elagolix.

DETAILED DESCRIPTION

Figure 1A:
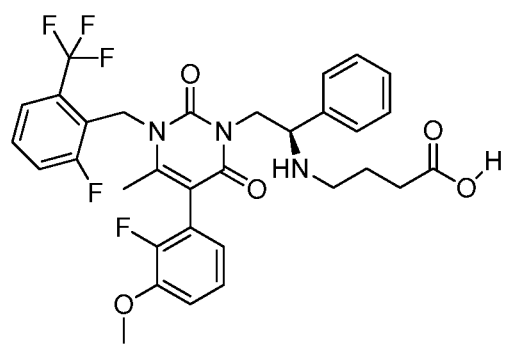
FIG. 1A shows the chemical structure of Elagolix.

The process according to the instant disclosure can significantly improve the material properties of a drug substance (i.e., a compound suitable for pharmaceutical purposes without the admixture of additional excipients), such as powder flow and handling with respect to the development of electrostatic charge. The ResonantAcoustic® mixing technology employed in this disclosure utilizes resonance phenomenon to efficiently transfer energy to the particles inside the vessel, leading to rapid fluidization of drug substance particles. The high velocity of the particles, the frequent collisions among the particles, and collisions between the particles and the vessel result in the granulation of the drug substance (i.e., size enlargement). This is similar to observations typical during a granulation process which require binders and granulation fluids. This disclosure is the first demonstration of an auto-granulation process using the ResonantAcoustic® mixing technology. The additional benefit of such improvements on drug substance properties is the ability to develop formulations with increased processability due to enhanced flow and/or larger particle size.

As used herein, the term "bulk drug substance" refers to a drug substance consisting of at least 90% w/w of the drug with no more than 10% w/w of pharmaceutical excipients or other materials. More specifically, bulk drug substance consists of at least 95% w/w drug substance with no more than 5% w/w of pharmaceutical excipients. Finally, the bulk substance consists of at least 99% w/w of drug substance with no more than 1% w/w of pharmaceutical excipients.

The following examples are being submitted to illustrate embodiments of the present disclosure. This disclosure is not to be limited to its representative examples. Parts and percentages are by weight unless otherwise indicated.

EXAMPLES

Elagolix drug substance was employed as an amorphous and hygroscopic solid having poor flowability (ffc<2), and low bulk density (<0.25 g/mL) and a variable particle size distribution due to the agglomeration of sub-micron primary particles.

ResonantAcoustic® mixing technology has recently been introduced as an alternative mixing technology for powders and liquids that allows for rapid, uniform dispersion of material. This process operates on the principle of resonance where low frequency, acoustic energy creates a homogenous shear field within a mixing vessel, and the energy is transferred directly to the material to produce a consistent mixture without impellers or other additional mixing aids (Mullarney, M. P.; Beach, L. E.; Langdon, B. A.; Polizzi, M. A., *Pharmaceutical Technology*, 2011, 35, 94-102).

Example 1

The feasibility of using acoustic mixing to improve the poor flow of Elagolix drug substance was assessed using a lab scale ResonantAcoustic® Mixer by varying the intensity and time of mixing. Mixing of neat Elagolix at 60% intensity up to 20 min and 80% up to 10 min resulted in large spherical granules, typical to what is observed during a wet granulation process. The intensity of mixing correlates with the accelerative force applied to the mixing vessel and a fortiori, the drug substance. Results shown in Table 1 demonstrate significant improvement in the flow properties of the drug substance. The greatest improvement in flow from ffc of 1.96 to 7.27 occurs after acoustic mixing at 80% intensity for 10 min, resulting in changing poor flowing material to free flowing material.

Figure 1B:
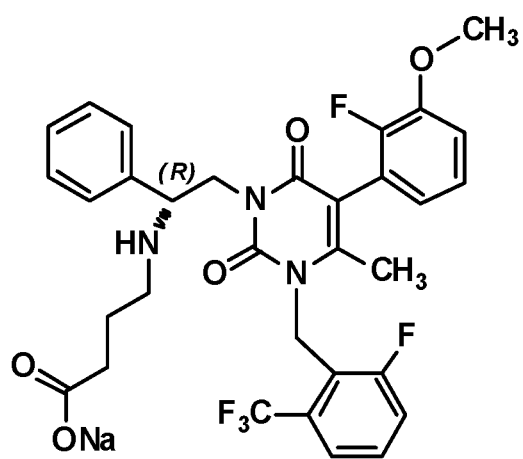
FIG. 1B shows the chemical structure of the monosodium salt of Elagolix.

Procedure—Dispense Elagolix sodium salt (FIG. 1B) drug substance in the acoustic mixing container sufficient to occupy a 50-80% fill volume. Allow the container to mix for the time periods indicated in the Table 1.

TABLE 1

Particle Size and Flow of Elagolix before and after Acoustic Mixing

| Run ID | Run Intensity (%) | Run Time (min) | Dv10 | Dv50 | Dv90 | ffc |
|---|---|---|---|---|---|---|
| As is | N/A | N/A | 21 | 337 | 815 | 1.96 |
| 1 | 40 | 8 | 154 | 432 | 939 | 2.50 |
| 2 | 40 | 16 | 144 | 405 | 853 | 2.10 |
| 3 | 60 | 4 | 143 | 383 | 842 | 2.40 |
| 4 | 60 | 8 | 112 | 298 | 720 | 2.80 |
| 5 | 60 | 16 | 270 | 469 | 795 | 3.96 |
| 6 | 80 | 6 | 237 | 512 | 954 | 3.21 |
| 7 | 80 | 10 | 281 | 629 | 1030 | 7.27 |

Example 2

The feasibility of using acoustic mixing to improve the poor flow of Elagolix drug substance was assessed using a lab scale Resodyn® Acoustic Mixer (LamRAM II) by varying the fill level, mixing time, and mixing intensity.

Procedure: Dispense Elagolix sodium salt drug substance in the acoustic mixing container sufficient to occupy the fill volume indicated below in Table 2. Allow the container to mix for the time period indicated in Table 2.

TABLE 2

Physical Properties of Elagolix Before and After Acoustic Mixing

| Mixing Time (min) | % Fill | Force (G) | Bulk Density (g/mL) | Flow (FFC) | Particle Size Distribution | | |
|---|---|---|---|---|---|---|---|
| | | | | | D(10) | D(50) | D(90) |
| 0 | 0 | 0 | 0.176 | | | | |
| 15 | 75 | 60 | 0.246 | 2.1 | 46.8 | 156 | 446 |
| 15 | 75 | 70 | 0.278 | 2.8 | 62.2 | 181 | 466 |
| 15 | 75 | 85 | 0.303 | 3.6 | 72.7 | 161 | 399 |
| 30 | 75 | 60 | 0.275 | 2.5 | 55.5 | 154 | 375 |
| 30 | 75 | 70 | 0.306 | 3.6 | 74.1 | 164 | 393 |
| 30 | 75 | 85 | 0.327 | 5.6 | 90.6 | 153 | 278 |
| 15 + 15 | 75 | 85 | 0.334 | 5.1 | 92.1 | 155 | 274 |
| 30 | 75 | 100 | 0.337 | 5.1 | 102 | 156 | 250 |
| 30 | 20 | 85 | 0.331 | 5.1 | 80.6 | 141 | 257 |
| 30 | 100 | 85 | 0.367 | 7.5 | 137 | 229 | 402 |
| 45 | 75 | 60 | 0.296 | 3.6 | 70.3 | 166 | 386 |
| 45 | 75 | 70 | 0.318 | 4.9 | 80.2 | 156 | 349 |
| 45 | 75 | 85 | 0.335 | 5.5 | 93.5 | 145 | 241 |
| 60 | 75 | 60 | 0.309 | 4.2 | 77.6 | 172 | 400 |
| 60 | 75 | 70 | 0.326 | 5.3 | 81.3 | 146 | 289 |
| 60 | 75 | 85 | 0.35 | 5.4 | 95.8 | 149 | 236 |

The invention claimed is:

1. A process comprising acoustically mixing a bulk drug substance consisting of at least 90% w/w drug substance and no more than 10% w/w of a pharmaceutical excipient or other material wherein said acoustic mixing comprises applying acoustic energy to a mixing vessel containing the drug substance for a time and at an intensity sufficient to form a granule.

2. The process according to claim 1 wherein an accelerative force of greater than 10 G is applied to the mixing vessel.

3. The process of claim 2 wherein said accelerative force is greater than 20 G.

4. The process of claim 3 wherein said accelerative force is greater than 40 G.

5. The process of claim 4 wherein said accelerative force is greater than 60 G.

6. The process of claim 5 wherein said accelerative force is greater than 80 G.

7. The process according to claim 1 wherein said drug substance comprises an amorphous solid.

8. The process according to claim 1 wherein said drug substance has a flowability constant of less than 5.

9. The process according to claim 1 wherein said drug substance has a flowability constant of less than 2.

10. The process according to claim 1 wherein prior to acoustic mixing, the drug substance has a flowability constant of less than 2 and subsequent to mixing greater than 2.

11. The process according to claim 1 wherein prior to acoustic mixing, the drug substance has a flowability constant of less than 1 and subsequent to mixing greater than 1.

12. The process according to claim 1 wherein the flowability constant is increased by at least 0.1.

13. The process according to claim 1 wherein the flowability constant is increased by at least 0.2.

14. The process according to claim 1 wherein the flowability constant is increased by at least 0.3.

15. The process according to claim 1 wherein the flowability constant is increased by at least 0.4.

16. The process according to claim 1 wherein the flowability constant is increased by at least 0.5.

17. The process according to claim 1 wherein prior to acoustic mixing said drug substance has a bulk density of less than 0.4 g/ml.

18. The process according to claim 1 wherein prior to acoustic mixing, the drug substance has a volume-averaged particle size DV10 of less than 100 μm.

19. The process according to claim 1 wherein acoustic mixing of the drug substance increases the volume-averaged particle size DV10 by at least 10 μm.

20. The process according to claim 1 wherein said drug substance is elagolix or elagolix monosodium salt.

21. A process comprising acoustically mixing a bulk drug substance consisting of at least 90% elagolix monosodium salt and no more than 10% of a pharmaceutical excipient or other material, wherein said acoustic mixing comprises applying acoustic energy to a mixing vessel containing the bulk drug substance for a time and at an intensity sufficient to produce a granule.

22. A granule comprising elagolix monosodium salt prepared by the process according to claim 21.

23. A pharmaceutical formulation comprising the granule of claim 22.

24. A process comprising acoustically mixing a bulk drug substance consisting of at least 90% amorphous elagolix monosodium salt and no more than 10% of a pharmaceutical excipient or other material, wherein said acoustic mixing comprises applying acoustic energy to a mixing vessel containing the bulk drug substance for a time and at an intensity sufficient to produce a granule.

25. A granule comprising elagolix monosodium salt prepared by the process according to claim 24.

26. A pharmaceutical formulation comprising the granule of claim 25.

\* \* \* \* \*